United States Patent
Kim et al.

(10) Patent No.: US 10,359,509 B2
(45) Date of Patent: Jul. 23, 2019

(54) IMAGE PROCESSOR, ULTRASONIC IMAGING DEVICE, AND IMAGE PROCESSING METHOD

(71) Applicant: SAMSUNG ELECTRONICS CO., LTD., Suwon-si (KR)

(72) Inventors: Kyu Hong Kim, Seongnam-si (KR); Sung Chan Park, Suwon-si (KR); Su Hyun Park, Hwaseong-si (KR); Joo Young Kang, Yongin-si (KR); Jung Ho Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 206 days.

(21) Appl. No.: 14/329,176

(22) Filed: Jul. 11, 2014

(65) Prior Publication Data

US 2015/0015720 A1 Jan. 15, 2015

(30) Foreign Application Priority Data

Jul. 11, 2013 (KR) ......................... 10-2013-0081650

(51) Int. Cl.
*A61B 8/00* (2006.01)
*A61B 8/13* (2006.01)
(Continued)

(52) U.S. Cl.
CPC ............ *G01S 7/52046* (2013.01); *A61B 8/00* (2013.01); *A61B 8/13* (2013.01); *G06T 1/60* (2013.01); *G06F 2212/00* (2013.01)

(58) Field of Classification Search
None
See application file for complete search history.

(56) References Cited

U.S. PATENT DOCUMENTS 5,980,459 A * 11/1999 Chiao .................. A61B 8/06
600/447
6,322,505 B1 * 11/2001 Hossack ................ A61B 8/00
600/437

(Continued)

FOREIGN PATENT DOCUMENTS

JP 2011-173008 A 9/2011
KR 10-0737040 B1 7/2007

OTHER PUBLICATIONS

Communication dated May 9, 2018 by the Korean Intellectual Property Office in counterpart Korean Patent Application No. 10-2013-0081650.

(Continued)

*Primary Examiner* — William C Vaughn, Jr.
*Assistant Examiner* — Lindsay J Uhl
(74) *Attorney, Agent, or Firm* — Sughrue Mion, PLLC

(57) ABSTRACT

Disclosed herein are an image processor, an ultrasonic imaging device, and an image processing method. The image processor includes a signal input unit configured to receive an input signal on a channel, a weighting coefficient database configured to store a weighting coefficient wherein the weighting coefficient is part of a weighting coefficient subgroup, and a processor configured to select the weighting coefficient subgroup from the weighting coefficient database, and convert the input signal by selecting and using the weighting coefficient from the weighting coefficient subgroup.

16 Claims, 11 Drawing Sheets

(51) Int. Cl.
*G01S 7/52* (2006.01)
*G06T 1/60* (2006.01)

(56) References Cited

U.S. PATENT DOCUMENTS

| | | | |
|---|---|---|---|
| 6,436,044 B1 | 8/2002 | Wang | |
| 6,584,165 B1* | 6/2003 | Wang | A61B 6/032 378/15 |
| 6,697,506 B1* | 2/2004 | Qian | G06T 7/0012 382/128 |
| 2006/0034279 A1* | 2/2006 | Cho | H04B 7/0617 370/390 |
| 2008/0048911 A1 | 2/2008 | Sumi | |
| 2009/0299184 A1* | 12/2009 | Walker | G01S 7/52046 600/447 |
| 2010/0305441 A1 | 12/2010 | Lin et al. | |
| 2012/0147959 A1* | 6/2012 | Amano | H04N 19/61 375/240.16 |
| 2013/0253325 A1* | 9/2013 | Call | G01S 15/8952 600/447 |

OTHER PUBLICATIONS

Communication dated Nov. 29, 2018, issued by the Korean Intellectual Property Office in counterpart Korean Patent Application No. 10-2013-0081650.
Communication dated Feb. 22, 2019, issued by the Korean Intellectual Property Office in counterpart Korean Patent Application No. 10-2013-0081650.

* cited by examiner

IMAGE PROCESSOR, ULTRASONIC IMAGING DEVICE, AND IMAGE PROCESSING METHOD

CROSS-REFERENCE TO RELATED APPLICATION

This application claims priority from Korean Patent Application No. 10-2013-0081650, filed on Jul. 11, 2013 in the Korean Intellectual Property Office, the disclosure of which is incorporated herein by reference in its entirety.

BACKGROUND

1. Technical Field

Systems, methods, and apparatuses consistent with exemplary embodiments relate to an image processor, an ultrasonic imaging device, and an image processing method.

2. Description of the Related Art

Devices such as an acoustic detector, an ultrasonic imaging device, a sonar acoustic detector, or a radar system may receive an external sound wave, ultrasonic wave, or electromagnetic wave, and may generate an ultrasound image or radar image using the received sound wave, ultrasonic wave, or electromagnetic wave.

When an image is generated using the received sound wave, ultrasonic wave, or electromagnetic wave, the acoustic detector, ultrasonic imaging device, or radar may allow collected sound wave signals, ultrasonic signals, or electromagnetic signals to be focused. In this case, the acoustic detector, ultrasonic imaging device, or radar may add a predetermined weight to each channel of the collected signals such that a signal falling within a specific area is emphasized and a signal falling within another area is relatively attenuated, and may focus the ultrasonic signal. Accordingly, it is possible to obtain an image for subject diagnosis.

Beamforming may be used to form a beam. A data-independent beamforming method and/or an adaptive beamforming method may be implemented according to characteristics of a weight added to each ultrasonic signal within an ultrasonic wave channel.

The data-independent beamforming method may use a weight determined independently from an input ultrasonic signal, and is also called fixed beamforming due to a fixed weight.

The adaptive beamforming method may determine an optimal weight according to the input ultrasonic signal. In the adaptive beamforming method, a weight used for beamforming may be changed according to the input ultrasonic signal. The adaptive beamforming is also called data-dependent beamforming.

SUMMARY

According to an aspect of an exemplary embodiment, there is provided an image processor including a signal input unit configured to receive an input signal on a channel, a weighting coefficient database configured to store a weighting coefficient wherein the weighting coefficient is part of a weighting coefficient subgroup, and a processor configured to select the weighting coefficient subgroup from the weighting coefficient database, and convert the input signal by selecting and using the weighting coefficient from the weighting coefficient subgroup.

The image processor may further include a storage configured to store the weighting coefficient subgroup selected from the weighting coefficient database.

The storage may be a cache memory.

The processor may be further configured to store the weighting coefficient subgroup selected from the weighting coefficient database in the storage, and convert the input signal by selecting and using the weighting coefficient from the weighting coefficient subgroup stored in the storage when image processing is performed.

The image processor may be further configured to select the weighting coefficient subgroup from the weighting coefficient database based on at least one of an external input and a condition.

The condition may be at least one of an image capture mode, an image processing method, and input signal characteristics.

The processor may be further configured to select the weighting coefficient, for input signals of some channels among input signals of at least one channel, from the weighting coefficient subgroup, and convert the input signals of some channels.

According to an aspect of another exemplary embodiment, there is provided an ultrasonic imaging device including an ultrasound probe configured to receive an echo ultrasonic wave on a channel from a subject, and convert the received echo ultrasonic wave into an ultrasonic signal of the channel, a weighting coefficient database configured to store a plurality of weighting coefficients wherein at least one of the plurality of weighting coefficients corresponds to a weighting coefficient subgroup, and an image processor configured to select the weighting coefficient subgroup from the weighting coefficient database, and convert the ultrasonic signal by selecting and using the at least one weighting coefficient from the weighting coefficient subgroup.

The ultrasonic imaging device may further include a storage configured to store the weighting coefficient subgroup selected from the weighting coefficient database.

The storage may be a cache memory.

The image processor may be further configured to store the weighting coefficient subgroup selected from the weighting coefficient database in the storage, and convert the input signal by selecting and using the at least one weighting coefficient from the weighting coefficient subgroup stored in the storage when image processing is performed.

The at least one weighting coefficient may be at least one of a beamforming coefficient, a conversion filter, and a point spread function.

The image processor may be further configured to select at least one weighting coefficient subgroup from the weighting coefficient database based on at least one of an external input and a condition.

The condition may be at least one of an ultrasound image capture mode, a beamforming method, a kind of a subject, a frequency of an ultrasonic wave, and a focus area of an ultrasonic wave.

The image processor may be further configured to select at least one weighting coefficient, for input signals of some channels among input signals of at least one channel, from the weighting coefficient subgroup, and convert the input signals of some channels.

According to an aspect of another exemplary embodiment, there is provided an image processing method including selecting a weighting coefficient subgroup from a weighting coefficient database in which the weighting coefficient subgroup includes a plurality of weighting coefficients configured to be used with input signals received over at least one channel are stored, receiving an input signal on at least one channel, and selecting at least one weighting coefficient from the plurality of weighting coefficients from the selected weighting coefficient subgroup and converting the input signal of at least one channel using the at least one weighting coefficient.

The image processing method may further include storing the weighting coefficient subgroup selected from the weighting coefficient database at least one of temporarily and permanently.

In the storing, the weighting coefficient subgroup may be stored in a cache memory.

In the selecting of the weighting coefficient subgroup, the weighting coefficient subgroup may be selected from the weighting coefficient database based on at least one of an external input and a condition.

The weighting coefficient may be at least one of a beamforming coefficient, a conversion filter, and a point spread function.

BRIEF DESCRIPTION OF THE DRAWINGS

These and/or other aspects will become more apparent and more readily appreciated from the following description of exemplary embodiments, taken in conjunction with the accompanying drawings of which.

DETAILED DESCRIPTION

Figure 1:
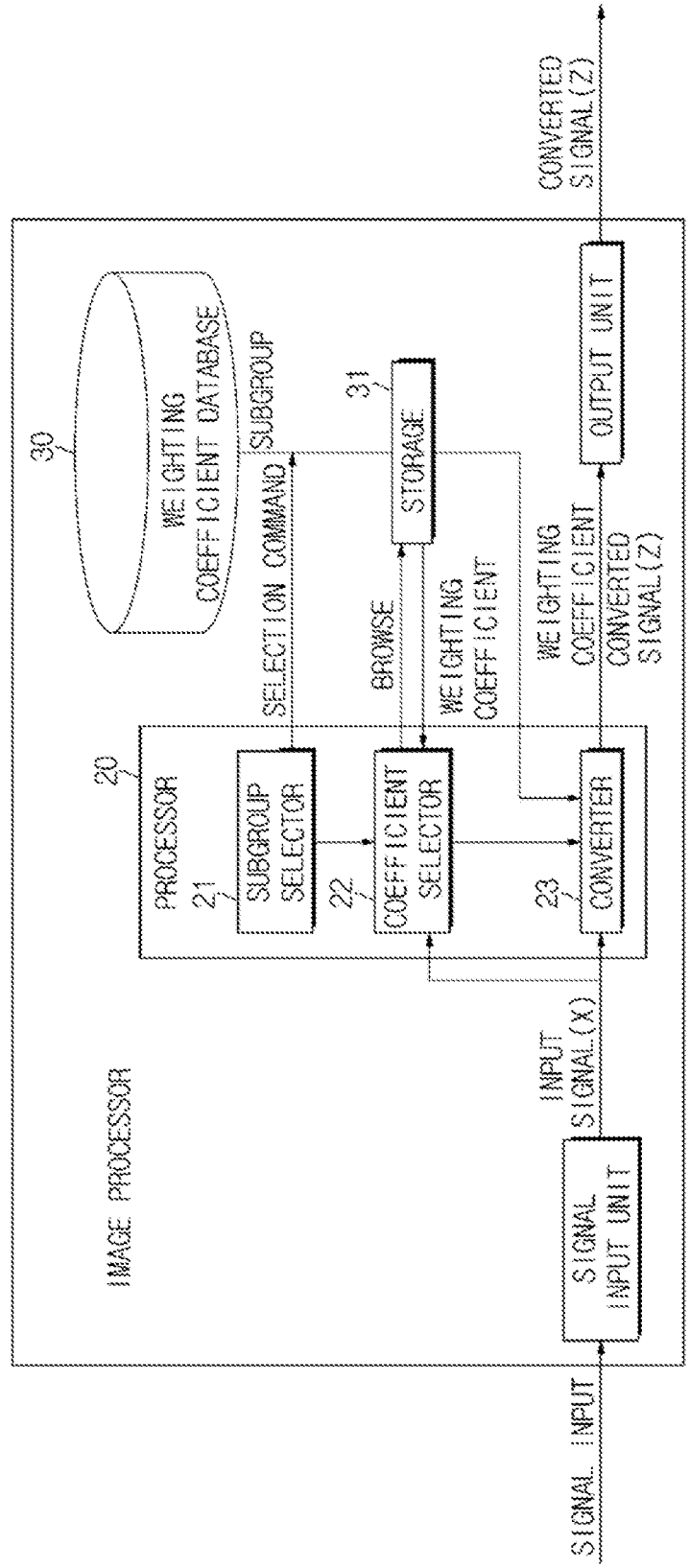
FIG. 1 is a diagram illustrating a configuration of an image processor according to an exemplary embodiment.

Reference will now be made in detail to the exemplary embodiments, examples of which are illustrated in the accompanying drawings, wherein like reference numerals refer to like elements throughout.

Hereinafter, an image processor according to one or more exemplary embodiments will be described with reference to FIGS. 1 to 4.

FIG. 1 is a diagram illustrating a configuration of the image processor according to the exemplary embodiment.

As illustrated in FIG. 1, the image processor may include a signal input unit 10, a processor 20, a weighting coefficient database 30, a storage 31, and an output unit 40.

The signal input unit 10 is configured to receive an input signal input from the outside and deliver the received input signal (x) to the processor 20. In this case, the input signal (x) input to the signal input unit 10 may be an input signal of at least one channel, or of a plurality of channels.

The input signal input to the signal input unit 10 may be a signal that is obtained by converting a predetermined sound wave or electromagnetic wave.

According to one or more exemplary embodiments, the input signal may be a signal that is obtained by converting an echo ultrasonic wave received from at least one target area inside a subject. In this exemplary embodiment, the echo ultrasonic wave may be a reflected ultrasonic wave of an emitted ultrasonic wave off of a target area inside the subject. Ann ultrasonic wave may be generated in at least one target area according to a laser emitted to at least one target area using, for example, a photoacoustic imaging system. According to another exemplary embodiment, a vibration elastic ultrasonic wave may be generated when ultrasonic waves having a plurality of different frequencies are emitted to at least one target area, and the at least one target area or a surrounding material thereof may be vibrated using, for example, an elastic ultrasonic wave imaging system.

Further, according to one or more exemplary embodiments, the input signal may be a signal that is obtained by converting a received microwave (ultra high frequency, a wavelength of 10 cm to 100 cm).

After a predetermined weighting coefficient is detected or a search score of the predetermined weighting coefficient is obtained, the processor 20 may convert the input signal using the obtained predetermined weighting coefficient or search score.

Specifically, according to an exemplary embodiment and as illustrated in FIG. 1, the processor 20 may include a subgroup selector 21, a coefficient selector 22, and a converter 23.

The subgroup selector 21 may select at least one subgroup of weighting coefficients from the weighting coefficient database 30.

Specifically, according to a processing condition input from a user, a pre-stored processing condition, or the input signal (x), the subgroup selector 21 selects at least one subgroup to be used for input signal (x) conversion from the weighting coefficient database 30.

In this case, the processing condition input from the user or the pre-stored processing condition may be, for example, an image capture mode, an image processing method, input signal characteristics, and/or a kind of the subject. In the case of an ultrasonic imaging device being used, the image capture mode may include various image capture modes, for example, an abdominal ultrasound imaging mode, a cardiac ultrasound imaging mode, and a breast ultrasound imaging mode. Moreover, the image processing method may be a method of generating or processing an image based on the input signal, for example, a beamforming method used in the ultrasonic imaging device or sonar. In this case, the beamforming method may be, for example, a scan line method or a plain wave method in the ultrasonic imaging device. The input signal characteristics may include a focal length, a frequency of an ultrasonic wave, a sound wave in the ultrasonic imaging device, or sonar.

The subgroup selector 21 may select at least one subgroup based on one processing condition or a plurality of processing conditions.

Figure 2:
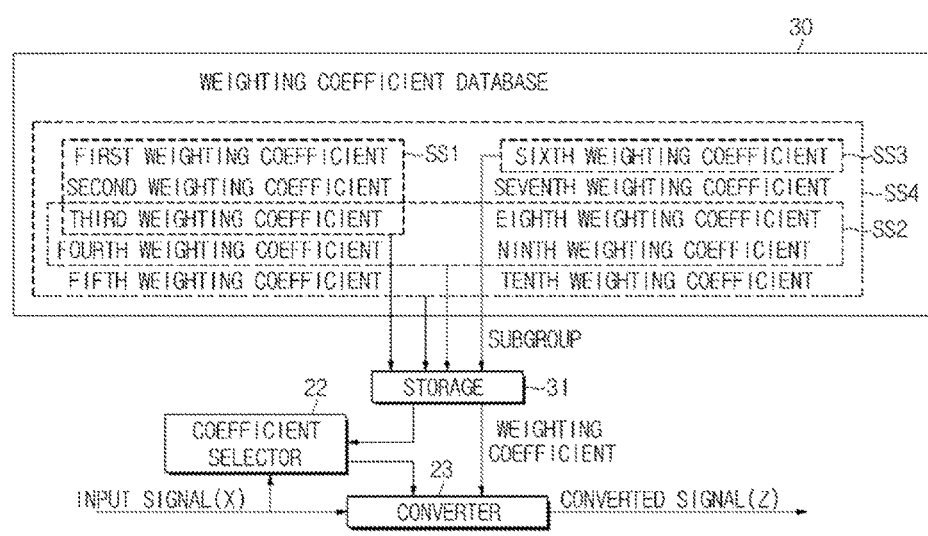
FIG. 2 is a diagram illustrating a configuration of a weighting coefficient database and a storage according to an exemplary embodiment.

FIG. 2 is a diagram illustrating a configuration of the weighting coefficient database and the storage according to an exemplary embodiment.

As illustrated in FIG. 2, the weighting coefficient database 30 may include at least one weighting coefficient. The weighting coefficient is a weight applied to an input signal of each channel when input signals of a plurality of channels input from the signal input unit 10 are converted.

The weighting coefficient stored in the weighting coefficient database 30 may be, for example, a beamforming coefficient, a conversion filter, or a point spread function. The weighting coefficient may also be a window function used in signal processing, that is, an apodization function.

As illustrated in FIG. 2, at least one weighting coefficient included in the weighting coefficient database 30 may configure at least one subgroup (subset, ss1 to ss4).

In this case, as illustrated in FIG. 2, each subgroup may include a plurality of weighting coefficients such as a first and second subgroups (ss1 and ss2), or may include a single weighting coefficient such as a third subgroup (ss3).

Moreover, one subgroup such as the first subgroup (ss1) and another subgroup such as the second subgroup (ss2) may include a weighting coefficient in common such as a third weighting coefficient. In other words, all or some subgroups among a plurality of subgroups of the weighting coefficient database 30 may include an overlapping weighting coefficient. Alternatively, each of the plurality of subgroups of the weighting coefficient database 30 may include only different non-overlapping weighting coefficient.

Furthermore, a specific subgroup among the plurality of subgroups, for example, a fourth subgroup (ss4) may include all weighting coefficients stored in the weighting coefficient database 30.

Each weighting coefficient of the weighting coefficient database 30 may be included in at least one subgroup among, for example, the first to fourth subgroups (ss1 to ss4). In some cases, a specific weighting coefficient among weighting coefficients of the weighting coefficient database 30 may not be included in any subgroups.

According to an exemplary embodiment, each subgroup of the weighting coefficient database 30 may be previously defined by, for example, a user or a system designer.

In other words, the user or system designer may define at least one subgroup including at least one weighting coefficient in advance. Specifically, the user or system designer may define at least one subgroup by selecting at least one weighting coefficient from among the plurality of weighting coefficients stored in the weighting coefficient database 30. Alternatively, the user or system designer may define at least one subgroup including at least one weighting coefficient, and then build the weighting coefficient database 30 using the defined subgroup.

The user or system designer may define at least one subgroup using various figures that are empirically or statistically obtained, for example, weighting coefficient usage frequency.

Moreover, the user or system designer may define at least one subgroup according to various environment conditions of the input signal, for example, an ultrasound imaging target, a depth of focus, and a beamforming method, in case of the ultrasonic imaging device.

In this way, each subgroup of the weighting coefficient database 30 may be defined by the user or system designer, and the subgroup selector 21 may select at least one subgroup among the predefined subgroups.

According to another exemplary embodiment, each subgroup of the weighting coefficient database 30 may be defined by the subgroup selector 21. Specifically, when the subgroup selector 21 selects a predetermined subgroup, the subgroup selector 21 may extract at least one weighting coefficient from the weighting coefficient database 30, generate at least one subgroup including the at least one extracted weighting coefficient, and select at least one subgroup of weighting coefficients by selecting the at least one generated subgroup.

In this case, the subgroup selector 21 may select at least one subgroup by extracting at least one weighting coefficient according to the user input condition, pre-stored condition, or input signal (x).

The subgroup selector 21 may generate a subgroup of weighting coefficients by extracting weighting coefficients based on empirical or statistical figures, and then select the generated subgroup. In this case, the empirical and statistical figures may be, for example, usage frequency of weighting coefficients used in previously performed image conversion.

Moreover, in an exemplary embodiment that implements an ultrasonic imaging device, the subgroup selector 21 may generate at least one subgroup according to various environmental conditions, for example, an ultrasound imaging target, a depth of focus, and a beamforming method. In this case, the various environmental conditions may be input by, for example, the user or detected by sensors of the ultrasound imaging device.

Figure 3:
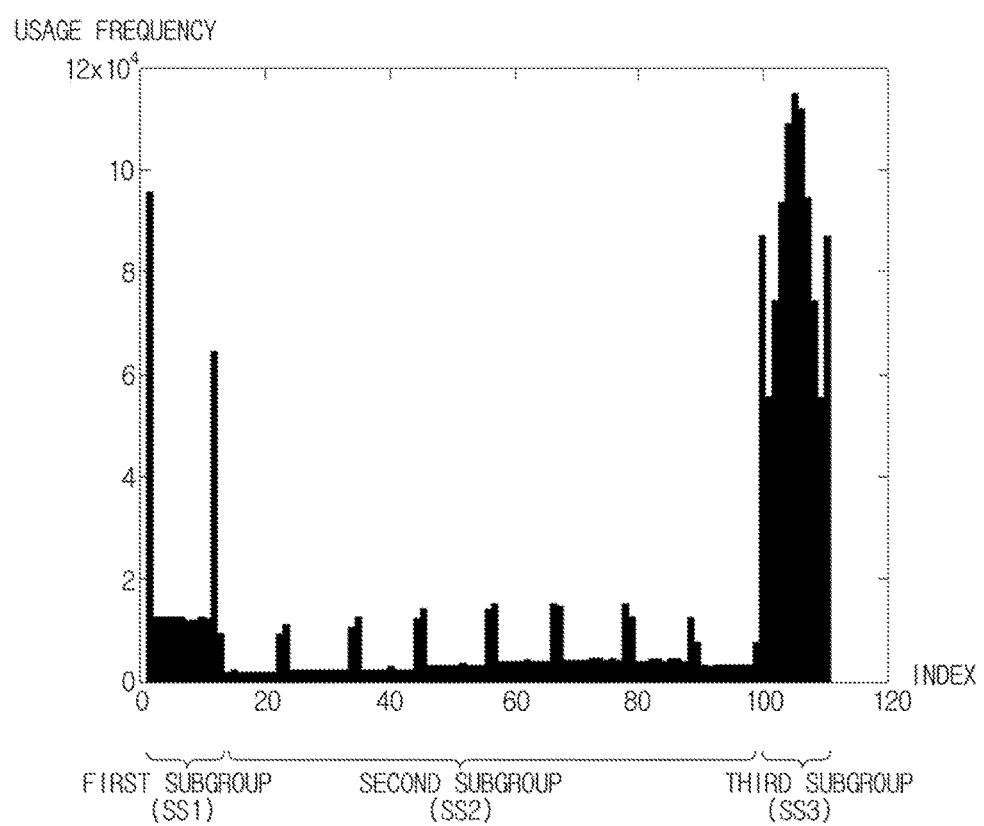
FIG. 3 is a diagram illustrating an example of apodization window usage frequency.

FIG. 3 is a histogram illustrating an example of apodization window usage frequency under constant conditions.

In FIG. 3, x-axis represents an index number to identify a plurality of apodization windows, and y-axis represents each usage frequency of the plurality of apodization windows. According to an exemplar embodiment, a weighting coefficient database, similar to the weighting coefficient data base 30 of FIG. 2, is built with the plurality of apodization windows illustrated on the x-axis of FIG. 3.

As shown, when an optimal apodization window is selected in order to convert an input signal under constant conditions, not all apodization windows are selected at a same usage proportion. Particularly, some of the apodization windows are frequently selected and used for input signal conversion as illustrated in FIG. 3. As illustrated in FIG. 3, for example, apodization windows having the index number of 0, 10, and 100 to 112 are more frequently selected and used as compared with the other apodization windows.

Therefore, an apodization window to be used for conversion may not be detected and therefore selected from among all apodization windows stored in the weighting coefficient database 30. Rather, an apodization window to be used for conversion may be detected and selected from among some of the apodization windows, for example, apodization windows included in a specific subgroup having high usage frequency. In this case, it may be possible to detect the optimal apodization window appropriate for input signal (x) conversion.

The subgroup selector 21 may select at least one subgroup including, for example, all weighting coefficients stored in the weighting coefficient database 30, some weighting coefficients among all apodization windows, or some apodization windows. Moreover, some weighting coefficients such as some apodization windows are extracted, and at least one subgroup including the some extracted apodization windows may be selected.

As illustrated in FIG. 3, among the plurality of apodization windows, a subgroup including a plurality of apodization windows having the index number of 0 to 10 is a first subgroup (ss1), a subgroup including a plurality of apodization windows having the index number of 11 to 99 is a second subgroup (ss2), and a subgroup including a plurality of apodization windows having the index number of 100 to 112 is a third subgroup (ss3). According to input or defined conditions, or the input signal (x), usage frequency of each apodization window within each subgroup (ss1 to ss3) may be given as in FIG. 3.

Thus, the subgroup selector 21 may select one subgroup which is the most frequently used among the plurality of subgroups such as the first to third subgroups (ss1 to ss3), that is, the third subgroup (ss3).

Moreover, the subgroup selector 21 may select at least one subgroup by extracting an apodization window having high frequency among the plurality of apodization windows. As illustrated in FIG. 3, for example, the third subgroup (ss3) may be selected by extracting a plurality of apodization windows corresponding to the third subgroup (ss3). In this case, the at least one selected subgroup may vary according to a type or the number of apodization windows to be extracted.

According to the exemplary embodiment, the subgroup selector 21 may select a plurality of subgroups. For example, the first and third subgroups (ss1 and ss3) illustrated in FIG. 3 may be selected. In this case, a priority may be respectively assigned to the selected subgroups such as the first and third subgroups (ss1 and ss3). More specifically, because selection frequency of apodization windows in the third subgroup (s33) is higher than that in the first subgroup (ss1), the subgroups may be selected such that the third subgroup (ss3) has a higher priority and the first subgroup (ss1) has a lower priority. According to exemplary embodiments, no additional priority is respectively assigned to each of the subgroups such as the first and third subgroups (ss1 and ss3), and the subgroups may be selected in random.

According to an exemplary embodiment, the subgroup selected by, or the weighting coefficient extracted from, the subgroup selector 21 may be stored in the storage 31 as illustrated in FIGS. 1 and 2.

The storage 31 temporarily or permanently stores at least one subgroup selected by the subgroup selector 21, or at least one weighting coefficient extracted from the subgroup selector 21.

According to an exemplary embodiment, the storage 31 may be implemented by, for example, an integrated circuit memory including at least one semiconductor chip, a magnetic memory using a magnetic substance, or an optical memory using a laser light.

According to an exemplary embodiment, the storage 31 may be a cache memory. Specifically, the storage 31 temporarily stores predetermined data delivered from a memory device in which the weighting coefficient database 30 is stored, and enables a processor to perform predetermined data processing rapidly.

At least one subgroup or at least one weighting coefficient stored in the storage 31 may be delivered to the coefficient selector 22 or the converter 23.

The coefficient selector 22 may select a weighting coefficient to be used for input signal conversion. Moreover, the coefficient selector 22 may calculate a score of the weighting coefficient.

According to an exemplary embodiment, the coefficient selector 22 may detect and select at least one weighting coefficient from at least one subgroup. More specifically, the coefficient selector 22 may select at least one weighting coefficient appropriate for input signal (x) conversion among at least one subgroup or at least one weighting coefficient stored in the storage 31.

According to the exemplary embodiment, the coefficient selector 22 may select by searching for at least one weighting coefficient among at least one weighting coefficient of at least one subgroup according to the input signal (x). For example, the coefficient selector 22 may select and determine an optimal weighting coefficient to be used for input signal (x) conversion based on the input signal (x). According to another exemplary embodiment, the coefficient selector 22 may select a predetermined weighting coefficient from at least one weighting coefficient of at least one subgroup independently from the input signal (x).

Moreover, when a predetermined priority is assigned to each of the plurality of subgroups, the coefficient selector 22 may select one subgroup among the plurality of subgroups based on the assigned priority, and search for and select an appropriate weighting coefficient from the selected subgroup. When the appropriate weighting coefficient is not detected in the selected subgroup, a subgroup having a subsequent priority is selected, and the appropriate weighting coefficient may be detected in the selected subgroup having the subsequent priority.

The coefficient selector 22 may select the appropriate weighting coefficient from at least one weighting coefficient included in at least one subgroup using, for example, one of the following Equations 1 or 2.

$$\{w_c\} = \underset{all\, w_p}{\operatorname{argmin}} \sum_{k=-K}^{K} \left| \sum_{i=1}^{M} w_p[i] x_{n+k}[i] \right| \quad \text{Equation 1}$$

$$\{w_c\} = \underset{all\, w_p}{\operatorname{argmin}} \sum_{k=-K}^{K} \left| \sum_{i=1}^{M} w_p[i] x_{n+k}[i] \right|^2 \quad \text{Equation 2}$$

Here, $w_p[i]$ represents at least one weighting coefficient stored in the storage 31, and $w_c$ represents a weighting coefficient detected by a coefficient detecting unit 22a of the coefficient selector 22 among at least one weighting coefficient stored in the storage 31. p represents an index of each weighting coefficient. $x_{n+k}[i]$ represents an input signal (x), and i represents an index of each channel of the input signal (x). M represents a total number of channels of the input signal (x). k represents an axis direction smoothing parameter, and K represents an upper or lower limit of the axis direction smoothing parameter to obtain a plurality of beamforming coefficients that optimize beamforming calculation results of some input signals. Here, K may include 0.

As shown in Equation 1, the coefficient selector 22 may detect a weighting coefficient $w_c$ that can minimize a sum of absolute values of the input signal (x) to which a predetermined weighting coefficient is added with respect to the input signal (x) of at least one channel. Moreover, as shown in Equation 2, the coefficient selector 22 may detect a weighting coefficient $w_c$ that can minimize a sum of absolute values of squares of the input signal (x) to which a predetermined weighting coefficient is added. In this case, the coefficient selector 22 may detect a weighting coefficient $w_c$ that can satisfy the above Equations 1 and 2 among a plurality of weighting coefficients $w_p$ stored in the storage 31.

The coefficient selector 22 may select the appropriate weighting coefficient using one of the above Equations 1 and 2. The coefficient selector 22 may select the appropriate weighting coefficient using both of the Equations 1 and 2. The weighting coefficient $w_c$ selected by the coefficient selector 22 is delivered to the converter 23 and may be used for input signal (x) conversion.

According to another exemplary embodiment, the coefficient selector 22 may calculate a search score of at least one weighting coefficient among weighting coefficients included in at least one subgroup.

In this case, the coefficient selector 22 may calculate the search score of at least one weighting coefficient included in at least one subgroup stored in the storage 31 using, for example, the following Equations 3 and 4.

$$\{S_c\} = \min_{all\, w_p} \sum_{k=-K}^{K} \left| \sum_{i=1}^{M} w_p[i] x_{n+k}[i] \right| \quad \text{Equation 3}$$

$$\{S_c\} = \min_{all\, w_p} \sum_{k=-K}^{K} \left| \sum_{i=1}^{M} w_p[i] x_{n+k}[i] \right|^2 \quad \text{Equation 4}$$

Here, $S_c$ represents the search score. Other than $S_c$, meanings of each letter and sign of Equations 3 and 4 are the same as in Equations 1 and 2.

As shown in Equation 3, the search score $S_c$ which is a value on a left-hand side of Equation 3 represents a sum of product of the weighting coefficient $W_c$ obtained by Equation 1 and the input signal (x) corresponding to the obtained weighting coefficient $W_c$, that is, a value that minimizes an absolute value of a weighted sum of the weighting coefficient $W_c$ and the input signal (x). That is, the search score may be a value that minimizes a weighted sum of the weighting coefficient and the input signal, or may be defined as a weighted sum of the input signal and the weighting coefficient calculated by the selected weighting coefficient.

As shown in Equation 4, the search score $S_c$ which is a value of a left-hand side of Equation 4 represents a sum of squares of product of the weighting coefficient $W_c$ obtained by Equation 2 and the input signal (x) corresponding to the obtained weighting coefficient $W_c$, that is, a value that minimizes a square of an absolute value of a weighted sum of the weighting coefficient $W_c$ and the input signal (x).

The coefficient selector 22 may calculate the search score $S_c$ using one of the above Equations 3 and 4. The coefficient selector 22 may use both of the Equations 3 and 4. Moreover, the coefficient selector 22 may calculate the search score $S_c$ using Equation used for selecting the weighting coefficient. Particularly, when the weighting coefficient $W_c$ is selected using, for example, Equation 1, the coefficient selector 22 may calculate the search score $S_c$ using a corresponding Equation, that is, Equation 3.

According to an exemplary embodiment, the coefficient selector 22 may calculate the search score $S_c$ of the weighting coefficient $W_c$ of all subgroups stored in the storage 31, and may calculate the search score $S_c$ of the weighting coefficient $W_c$ of a specific subgroup. Moreover, according to an exemplary embodiment, the coefficient selector 22 may calculate the search score $S_c$ of all weighting coefficients $W_c$ in at least one subgroup, or may calculate the search score $S_c$ of some weighting coefficients $W_c$.

The above-described search score $S_c$ may be naturally derived from operations of calculating the weighting coefficient $W_c$ according to Equations 1 and 2. The calculated search score $S_c$ may be delivered to the converter 23.

According to the exemplary embodiment, the converter 23 may convert the input signal (x) using at least one weighting coefficient selected by the coefficient selector 22.

For example, when the input signal (x) of a plurality of channels is input, the converter 23 may focus the input signal (x) of a plurality of channels using the at least one selected weighting coefficient, and output a converted signal (z) corresponding to the input signal (x) of a plurality of channels.

The converter 23 may generate the converted signal (z) by applying the weighting coefficient to the input signal (x) of at least one channel according to the following Equation 5.

$$z[n] = \sum_{m=0}^{M-1} w_m[n] x_m[n] \quad \text{Equation 5}$$

Here, z[n] represents a converted signal into which the input signal (x) is converted by the converter 23, and w represents a weighting coefficient selected by the coefficient selector 22. x represents the input signal. m represents an index of each channel of the input signal. Accordingly, $x_m[n]$ represents an input signal input through an mth channel, and $w_m[n]$ represents a weighting coefficient applied to the input signal of the mth channel. M represents a total number of channels of the input signal. n represents an index of the input signal. For example, when the input signal is input multiple times, n represents an index of each input signal. Specifically, $x_m[n]$ represents an input signal of the mth channel and input an nth time, and $w_m[n]$ represents a weighting coefficient applied to the input signal of the mth channel and input the nth time.

As shown in Equation 5, the converted signal (z) may be obtained by calculating a weighted sum of the input signal (x) and the weighting coefficient. In this case, as described above, the weighting coefficient may be at least one weighting coefficient selected from east one subgroup stored in the storage 31.

The converted signal (z) generated by the converter 23 may be delivered to the output unit 40.

According to another exemplary embodiment, the converter 23 may display the search score calculated by the coefficient selector 22 as a log scale, and output the converted signal (z) displayed as the log scale corresponding to the input signal (x). For example, in case of the ultrasonic imaging device, the converter 23 may display the search score Sc calculated by the coefficient selector 22 as the log scale, and obtain an ultrasound image having a B mode (brightness).

The output unit 40 may output the converted signal (z) to the outside.

Hereinafter, an image processing method according to an exemplary embodiment will be described with reference to FIG. 4.

Figure 4:
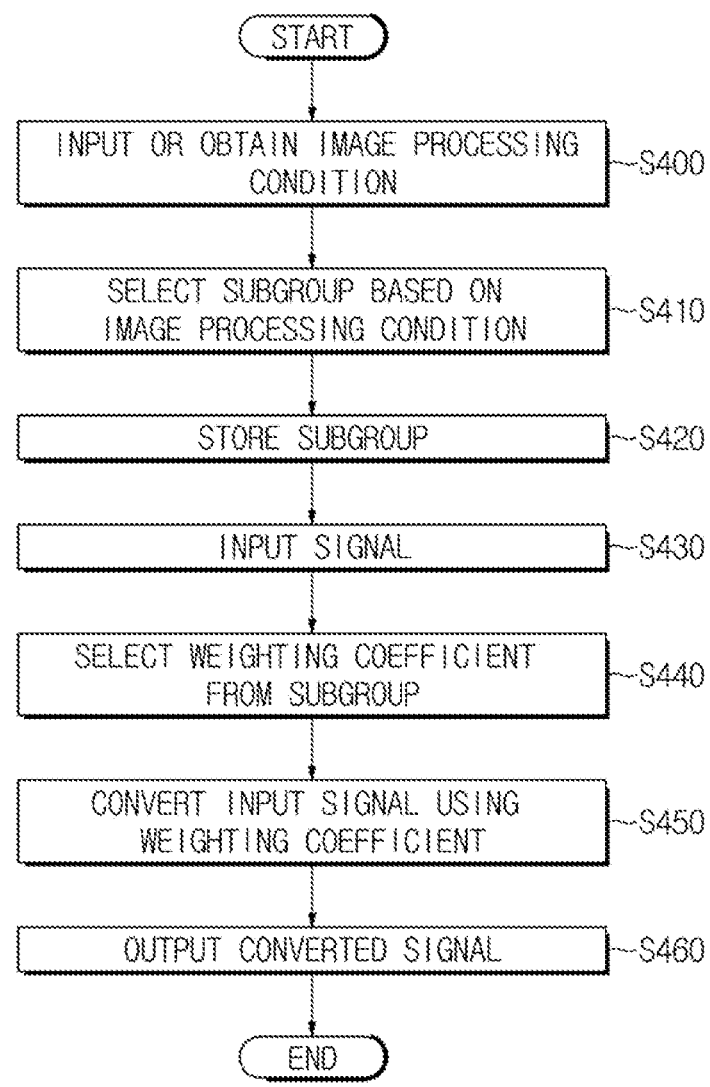
FIG. 4 is a flowchart illustrating an image processing method according to an exemplary embodiment.

FIG. 4 is a flowchart illustrating an image processing method according to an exemplary embodiment.

As illustrated in FIG. 4, in the image processing method according to the exemplary embodiment, a predetermined image processing condition is determined first by the user or predefined settings (s400). Specifically, the image processing condition may be input by the user through an external input unit, or may be delivered from a separate storage. In this case, the image processing condition may be at least one of an image capture mode, an image processing method, and input signal characteristics.

Based on the image processing condition, at least one subgroup is selected from at least one weighting coefficient (s410). The at least one selected subgroup may include at least one weighting coefficient. According to an exemplary embodiment, based on the image processing condition, at least one subgroup (for example a subgroup as shown in FIG. 2 or 3, specifically, subgroups ss1 to ss4) may be selected from the weighting coefficient database 30 that is built with at least one weighting coefficient.

The selected subgroup may be stored in a predetermined storage (s420). In this case, the storage may be implemented by an integrated circuit memory including at least one semiconductor chip, a magnetic memory using a magnetic substance, or an optical memory using a laser light. In addition, the storage may be a cache memory that is electrically connected to, for example, a central processor (CPU).

Subsequently, the input signal may be input (s430). Alternatively, the input signal may be input prior to operations s400 to s420. When the input signal is input prior to operation s410, at least one subgroup may be selected according to the input signal.

At least one weighting coefficient is selected and extracted from the selected subgroup (s440). That is, a predetermined weighting coefficient may be selected from at least one weighting coefficient in the selected subgroup. In this case, the selected weighting coefficient may be an appropriate weighting coefficient for the input signal (x) conversion. The above Equation 1 or 2 may be used to select the appropriate weighting coefficient.

When the appropriate weighting coefficient is selected, the input signal (x) may be converted using the selected weighting coefficient and the converted signal (z) may be obtained (s450). Specifically, the converted signal (z) may be obtained by a weighted sum of the selected weighting coefficient and the input signal (x). In this case, the above Equation 5 may be used.

The obtained converted signal (z) may be output to the outside (s460).

Hereinafter, an ultrasonic imaging device according to one or more exemplary embodiments will be described with reference to FIGS. 5 through 10.

An ultrasonic imaging device is a device that emits ultrasonic waves toward a target area inside a subject, collects ultrasonic waves reflected from the target area, and then obtains tomographic images of various tissues and structures inside the subject, for example, tomographic images of soft tissues or images of the bloodstream, using information on the collected ultrasonic waves.

According to an exemplary embodiment, an ultrasonic imaging device emits a laser toward a target area inside the subject, allows a substance of the target area inside the subject to vibrate, receives an ultrasonic wave generated at the substance of the target area according to substance vibration, and obtains an ultrasound image inside the subject. Moreover, the ultrasonic imaging device emits ultrasonic waves having different frequencies toward a target area inside the subject, receives a vibration wave generated by vibrating the substance of the target area or a substance surrounding thereof, and obtains images inside the subject.

Because such an ultrasonic imaging device may have a smaller size and may be cheaper than other imaging devices, and may display images in real time, it may be possible to use in various fields such as industry or medical.

Figure 5:
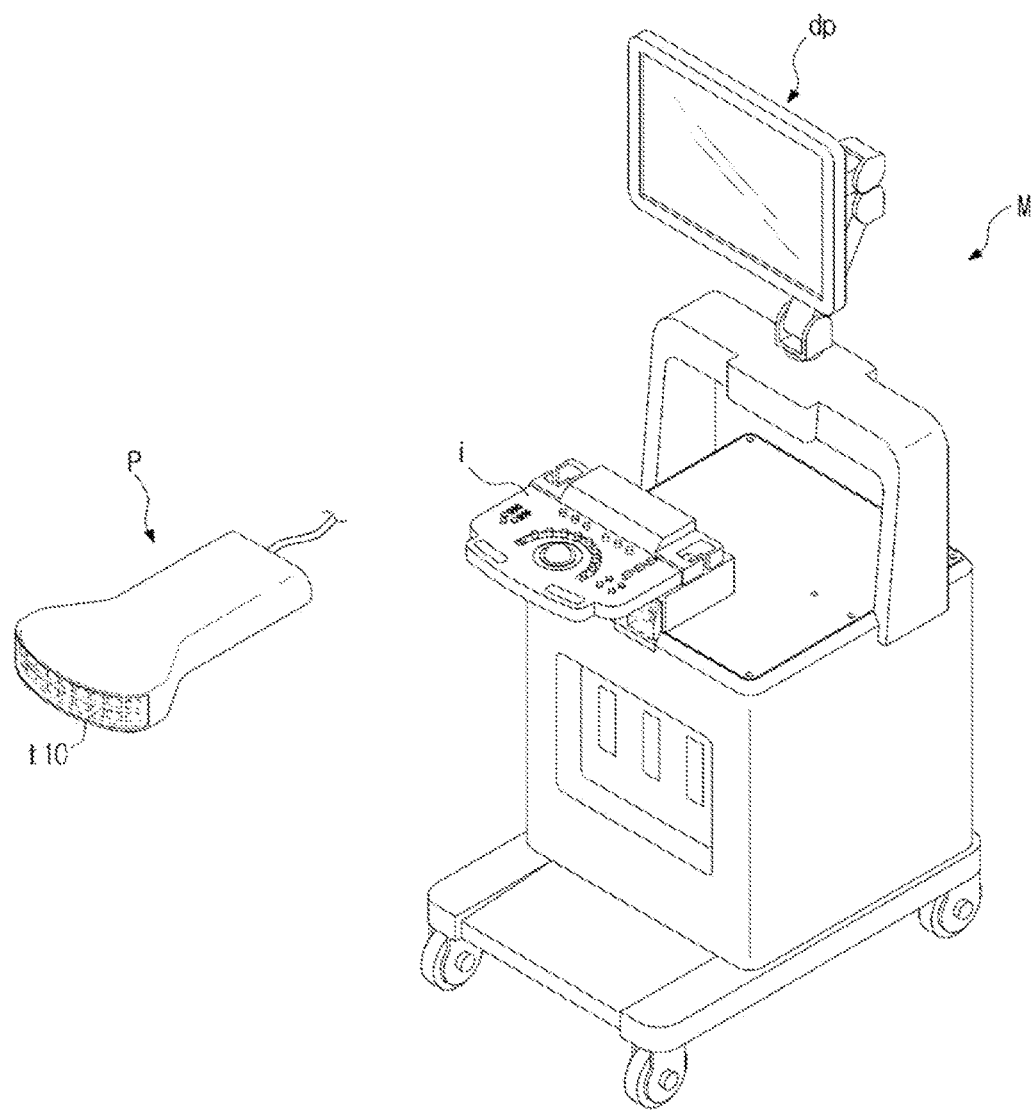
FIG. 5 is a perspective view of an ultrasonic imaging device according to an exemplary embodiment.
Figure 6:
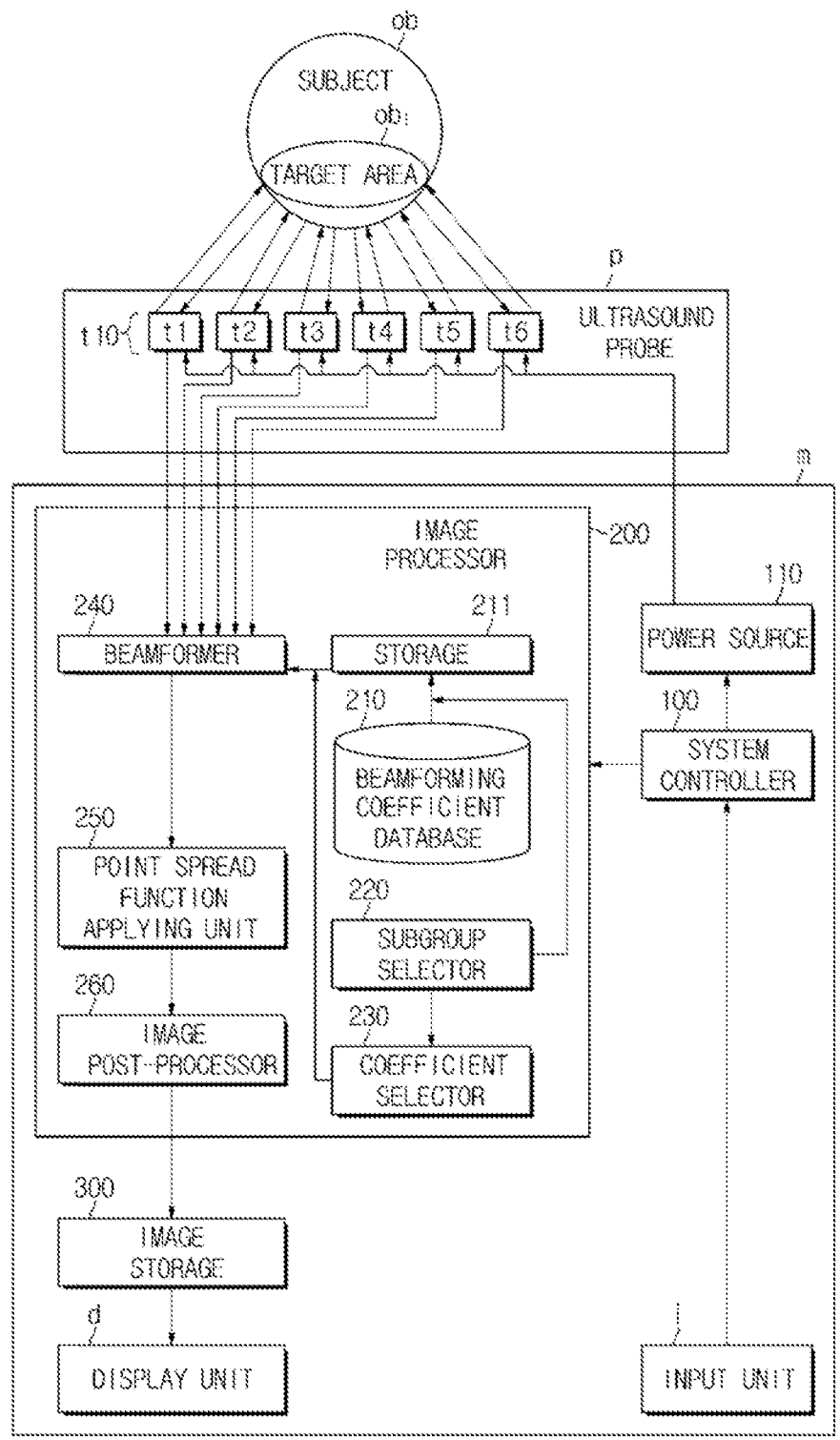
FIG. 6 is a diagram illustrating a configuration of the ultrasonic imaging device according to an exemplary embodiment.

FIG. 5 is a perspective view of the ultrasonic imaging device according to an exemplary embodiment. FIG. 6 is a diagram illustrating a configuration of the ultrasonic imaging device according to the exemplary embodiment.

As illustrated in FIGS. 5 and 6, the ultrasonic imaging device may include an ultrasound probe (p) configured to emit an ultrasonic wave toward the subject, receive an ultrasonic wave reflected at the target area inside the subject, and convert the received ultrasonic wave into an electrical signal, that is, an ultrasonic signal, and a main body unit (m) configured to generate an ultrasound image based on the ultrasonic signal output from the ultrasound probe (p).

Figure 7:
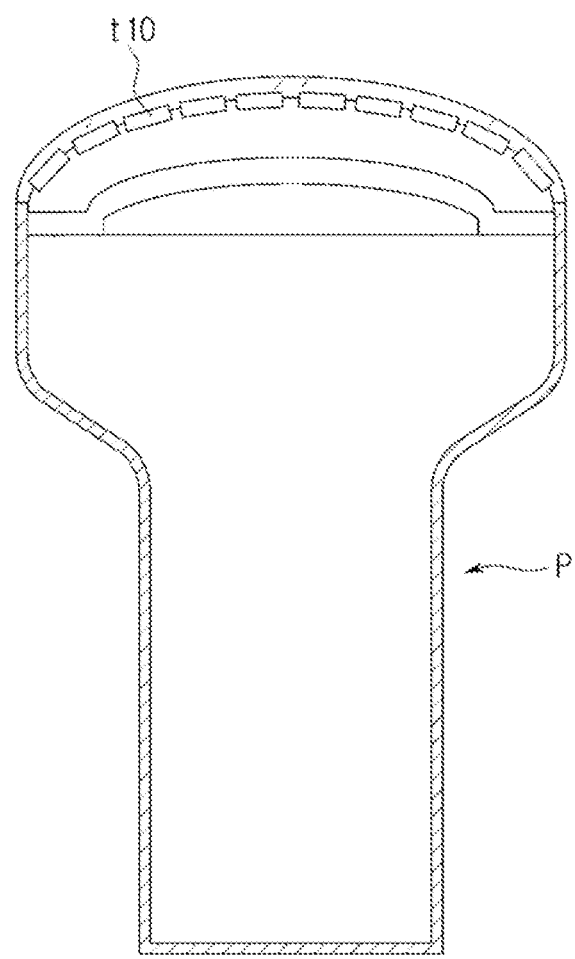
FIG. 7 is a diagram illustrating a configuration of an ultrasound probe according to an exemplary embodiment.

FIG. 7 is a diagram illustrating a configuration of the ultrasound probe according to an exemplary embodiment.

As illustrated in FIGS. 5 to 7, the ultrasound probe (p) may include at least one ultrasonic wave element (t10, t1 to t6). The ultrasonic wave element (t10) generates a predetermined ultrasonic wave based on an applied current, and outputs a predetermined current according to the received ultrasonic wave.

Specifically, the ultrasonic wave element (t10) may vibrate at a vibration frequency corresponding to a frequency of an AC current applied according to the AC current having a predetermined frequency applied from the outside. While the ultrasonic wave element (t10) vibrates at the vibration frequency, an ultrasonic wave having a frequency corresponding to the vibration frequency may be generated. The generated ultrasonic wave may be emitted toward a target area (ob1) inside a subject (ob).

When an ultrasonic wave having a predetermined frequency generated in at least one target area (ob1) arrives, the ultrasonic wave element (t10) may vibrate at a predetermined frequency corresponding to the frequency of the arrived ultrasonic wave. The vibrating ultrasonic wave element (t10) outputs an AC current having a frequency corresponding to the vibration frequency of the ultrasonic wave element (t10), and converts the ultrasonic wave into a predetermined electrical signal.

According to an exemplary embodiment, each ultrasonic wave element (t10, t1 to t6) of the ultrasound probe (p) may generate and receive an ultrasonic wave. According to another exemplary embodiment, among ultrasonic wave elements of the ultrasound probe (p), some ultrasonic wave elements may only generate an ultrasonic wave, and other ultrasonic wave elements may only receive an ultrasonic wave.

The ultrasonic wave element (t10) may be, for example, an ultrasonic transducer. The ultrasonic transducer is an element that converts a predetermined form of energy into another form of energy, for example, an electrical signal into acoustic energy, or acoustic energy back into an electrical signal. Examples of the ultrasonic transducer may include a piezoelectric ultrasonic transducer using a piezoelectric effect of a piezoelectric material, a magnetostrictive ultrasonic transducer that converts wave energy and electrical energy using a magnetostrictive effect of a magnetic substance, and a capacitive micromachined ultrasonic transducer (cMUT) that transmits and receives an ultrasonic wave using vibration of several hundreds or thousands of micromachined thin films. Moreover, various types of transducers capable of generating an ultrasonic wave according to an electrical signal or generating an electrical signal according to an ultrasonic wave may be used as the above-described ultrasonic wave element (t10 or t1 through t6).

As illustrated in FIGS. 6 and 7, the ultrasound probe (p) may include a plurality of ultrasonic receiving elements (t10). In this case, because each ultrasonic wave element (t10) respectively receives an ultrasonic wave, converts the received ultrasonic wave into an electrical signal, and outputs the result, an ultrasonic receiving unit 120 outputs the electrical signal of a plurality of channels (c1 to c10).

As illustrated in FIG. 6, the main body unit (m) of the ultrasonic imaging device may include a system controller 100, a power source 110, an image processor 200, an image storage 300, a display unit (d), and an input unit (i).

The system controller 100 may control overall operations of, for example, the power source 110, the image processor 200, the image storage 300, and the display unit (d), of the ultrasonic imaging device.

The system controller 100 may control overall operations of the ultrasonic imaging device or operations of each component of the ultrasonic imaging device based on predetermined settings, generate a predetermined control command according to user instructions or commands input through the input unit (i) that is electrically connected to the system controller 100, and then deliver the predetermined control command to each component of the ultrasonic imaging device to control operations of the ultrasonic imaging device.

The input unit (i) receives various pieces of data or predetermined instructions or commands for ultrasonic imaging device control from the user. The input unit (i) may include a user interface, for example, a keyboard, a mouse, a trackball, a touchscreen, or a paddle.

The input unit (i) may receive, for example, instructions, commands, or selection for operations of the image processor 200, from the user. The input unit (i) may receive processing conditions, for example, an image capture mode, an image processing method, a position of focus, a frequency of an ultrasonic wave to be emitted, or a kind of the subject. In this case, the image capture mode may be an abdominal ultrasound imaging mode, a cardiac ultrasound imaging mode, and a breast ultrasound imaging mode. The image processing method may be a method of focusing an ultrasonic wave of a plurality of channels, that is, the beamforming method. In this case, the beamforming method may be, for example, a scan line imaging method or a plain wave imaging method.

According to the exemplary embodiment, as illustrated in FIG. 5, the input unit (i) may be provided in the ultrasonic imaging device. According to another exemplary embodiment, the input unit (i) may be provided in or connected to a separate workstation that is connected to the ultrasonic imaging device via a wired or wireless communication network.

When the user inputs an ultrasonic wave emission initiating command and a frequency of an ultrasonic wave to be emitted through the input unit (i), the system controller 100 generates a predetermined control command based on the ultrasonic wave emission initiating command and the input frequency, and delivers the predetermined control command to the power source 110.

The power source 110 may apply an AC current having a predetermined frequency to each of the ultrasonic wave elements (t1 to t6) according to the delivered control command. Each of the ultrasonic wave elements (t1 to t6) vibrates according to the applied AC current having the predetermined frequency as described above, and generates a predetermined ultrasonic wave. The generated ultrasonic wave is reflected at the target area (ob1), and the reflected echo ultrasonic wave may be received by the ultrasonic wave elements (t1 to t6) again. The ultrasonic wave elements (t1 to t6) that have received the reflected echo ultrasonic wave convert the received echo ultrasonic wave into an electrical signal, that is, the ultrasonic signal, and output the result. In this case, as illustrated in FIG. 7, the output ultrasonic signal may be output to a number of channels corresponding to the number of ultrasonic wave elements (t1 to t6) provided in the ultrasound probe (p).

The ultrasonic signal output from the ultrasonic wave elements (t1 to t6) may be delivered to the image processor 200.

As illustrated in FIG. 6, according to the exemplary embodiment, the image processor 200 may include a beamforming coefficient database 210, a storage 211, a subgroup selector 220, a coefficient selector 230, and a beamformer 240.

The beamforming coefficient database 210 may include at least one beamforming coefficient to be used for ultrasonic signal beamforming. As illustrated in FIG. 2, the beamforming coefficient database 210 may include at least one subgroup including at least one beamforming coefficient. Each subgroup may include one beamforming coefficient or a plurality of beamforming coefficients. Moreover, all or some subgroups among the plurality of subgroups may include an overlapping beamforming coefficient, or all subgroups may include different beamforming coefficients. A certain subgroup may include all beamforming coefficients of the beamforming coefficient database 210. At least one beamforming coefficient of the beamforming coefficient database 210 may be included in at least one subgroup. In some cases, there may be a beamforming coefficient that is not included in any subgroups.

According to an exemplary embodiment, each subgroup of the beamforming coefficient database 210 may be predefined by the user or the system designer. According to another exemplary embodiment, each subgroup of the beamforming coefficient database 210 may be defined by the subgroup selector 220 before beamforming is performed or while beamforming is performed.

According to an exemplary embodiment, as illustrated in FIG. 3, each subgroup may be defined using various figures that are empirically or statistically obtained with respect to beamforming coefficients, for example, usage frequency of beamforming coefficients. Each subgroup may be defined by various environment conditions, for example, a subject, a depth of focus, and a beamforming method.

The subgroup selector 220 may select at least one subgroup from the beamforming coefficient database 210.

According to an exemplary embodiment, the subgroup selector 220 may select at least one subgroup predefined by the user or the system designer, or select at least one subgroup by extracting at least one beamforming coefficient from the beamforming coefficient database 210.

According to an exemplary embodiment, the subgroup selector 220 may select at least one subgroup according to user input conditions, pre-stored conditions, or the ultrasonic signal delivered from the ultrasound probe (p). For example, when the user designates a frequency and a depth of focus of an ultrasonic wave to be emitted through the input unit (i), the subgroup selector 220 may select at least one subgroup corresponding to the frequency and the depth of focus of the ultrasonic wave to be emitted. The subgroup selector 220 may select at least one subgroup based on a single processing condition or a plurality of processing conditions. The ultrasonic wave subgroup selected by the subgroup selector 220 may be delivered to and stored in the storage 211.

When a new condition is provided, for example, when the user changes a center frequency or a depth of focus of an ultrasonic wave to be emitted, or an observation area through the input unit (i), the subgroup selector 220 may select a new subgroup. The new subgroup selected by the subgroup selector 220 may be delivered to and stored in the storage 211. In this case, an existing subgroup stored in the storage 211 may be deleted from or maintained in the storage 211.

The subgroup selector 220 may select a plurality of subgroups. In this case, a priority may be respectively assigned to the plurality of selected subgroups.

The storage 211 may temporarily or permanently store the at least one subgroup selected by the subgroup selector 220. The storage 211 may be implemented by, for example, an integrated circuit memory, a magnetic memory, or an optical memory. The storage may be a cache memory.

As described above, while the storage 211 stores the at least one subgroup, when the subgroup selector 220 selects at least one new subgroup, at least one pre-stored subgroup and at least one newly selected subgroup may be stored together, or only the at least one newly selected subgroup may be stored and the at least one pre-stored subgroup may be deleted.

According to the exemplary embodiment, the coefficient selector 230 may select and extract at least one beamforming coefficient to be used for beamforming from among at least one beamforming coefficient included in at least one subgroup stored in the storage 211.

The coefficient selector 230 may search for and select at least one weighting coefficient from at least one weighting coefficient of at least one subgroup. According to the exemplary embodiment, the coefficient selector 230 may further select a beamforming coefficient appropriate for ultrasonic signal beamforming based on the ultrasonic signal delivered from the ultrasound probe (p). Alternatively, the coefficient selector 230 may select at least one predetermined weighting coefficient independently from the ultrasonic signal.

When a predetermined priority is assigned to each of the plurality of subgroups, the coefficient selector 230 may select one subgroup from among the plurality of subgroups based on the assigned priority, and select an appropriate beamforming coefficient in the selected subgroup.

The coefficient selector 230 may select the appropriate beamforming coefficient for ultrasonic signal beamforming using the above Equation 1 or 2. That is, the coefficient selector 230 may select a beamforming coefficient that can minimize an absolute value, or a square value of a weighted sum of the beamforming coefficient and the ultrasonic signal.

The beamforming coefficient selected by the coefficient selector 230 may be delivered to the beamformer 240.

According to an exemplary embodiment, the coefficient selector 230 of the image processor 200 may calculate a predetermined search score of each beamforming coefficient. The coefficient selector 230 may calculate the search score of each beamforming coefficient using, for example, the above Equation 3 or 4.

Figure 8:
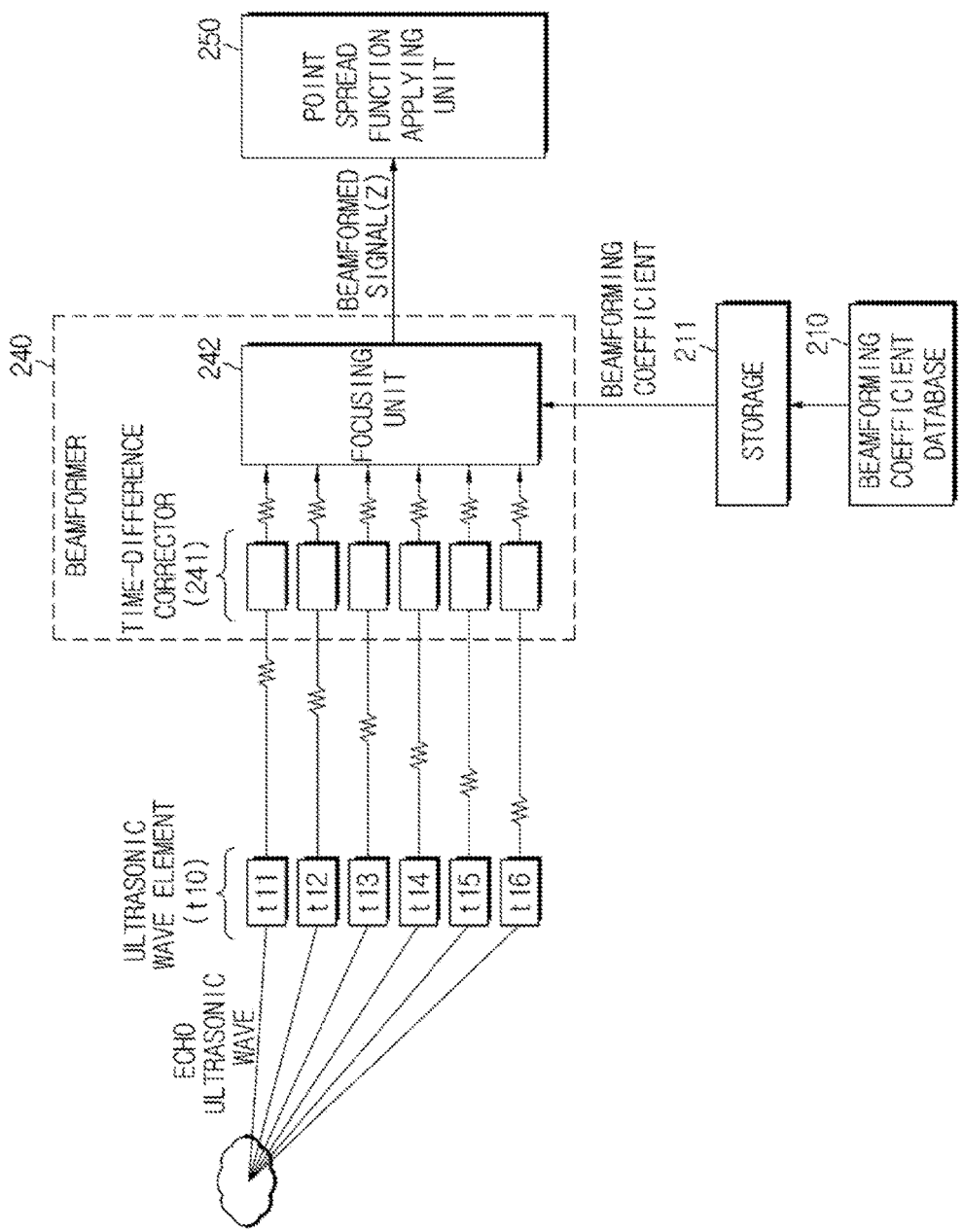
FIG. 8 is a diagram illustrating a configuration of a beamformer according to an exemplary embodiment.

FIG. 8 is a diagram illustrating a configuration of the beamformer according to an exemplary embodiment.

As illustrated in FIG. 8, the beamformer 240 may include a time-difference corrector 241, and a focusing unit 242.

The time-difference corrector 241 corrects a time difference between ultrasonic signals of a plurality of channels output from each ultrasonic wave element (t11 to t16). When each ultrasonic wave element (t11 to t16) receives an echo ultrasonic wave from the same target area inside the subject, a distance between the target area and each ultrasonic wave element (t11 to t16) is different, but a rate of the echo ultrasonic wave is generally constant. As a result, although the echo ultrasonic wave is reflected at the same target area at the same time, each ultrasonic wave element (t11 to t16) may receive the echo ultrasonic wave at a different time. Therefore, a certain amount of time difference may exist between ultrasonic signals output from each ultrasonic wave element (t11 to t16). The time-difference corrector 241 may correct the time difference between ultrasonic signals output from each ultrasonic wave element (t11 to t16).

For example, the time-difference corrector 241 may correct the time difference between ultrasonic signals such that the ultrasonic signal output from each ultrasonic wave element (t11 to t16) is delayed by a certain amount of time and is delivered to the focusing unit 242.

The focusing unit 242 focuses the ultrasonic signal of at least one channel, and generates and outputs a beamformed signal (z). In this case, the focusing unit 242 may focus the ultrasonic signal using the following Equation 6.

$$z[n] = \sum_{m=0}^{M-1} w_m[n] x_m[n - \Delta_m[n]]$$ Equation 6

Here, z[n] represents a beamformed signal. m represents an index of each channel of the ultrasonic signal, and M represents a total number of channels of the input signal. $x_m[n]$ represents an ultrasonic signal input through an mth channel. $w_m[n]$ represents a beamforming coefficient applied to the ultrasonic signal of the mth channel. n represents an index of a depth of the target area. $\Delta_m$ is a time delay value that is applied in the above time-difference corrector 241.

According to the exemplary embodiment, as illustrated in FIG. 8, the focusing unit 242 receives at least one beamforming coefficient from the storage 211, and focuses the ultrasonic signals using the at least one received beamforming coefficient. In this case, the at least one beamforming coefficient received from the storage 211 may be the beamforming coefficient selected by the above coefficient selector 230. The coefficient selector 230 may select at least one beamforming coefficient among at least one beamforming coefficient of at least one subgroup stored in the storage 211 as described above. Moreover, at least one subgroup may be a subgroup including at least one beamforming coefficient selected from the beamforming coefficient database 210 by the subgroup selector 220.

As illustrated in FIG. 8, the focusing unit 242 may focus ultrasonic signals of all channels using the beamforming coefficient delivered from the storage 211. Alternatively, the focusing unit 242 may focus ultrasonic signals of some channels using the beamforming coefficient delivered from the storage 211.

In addition, the focusing unit 242 may focus the ultrasonic signal using a single beamforming coefficient, or a plurality of beamforming coefficients. Moreover, among ultrasonic signals of a plurality of channels, ultrasonic signals of some channels may be focused using a predetermined beamforming coefficient, and ultrasonic signals of other channels may be focused using another beamforming coefficient.

Figure 9:
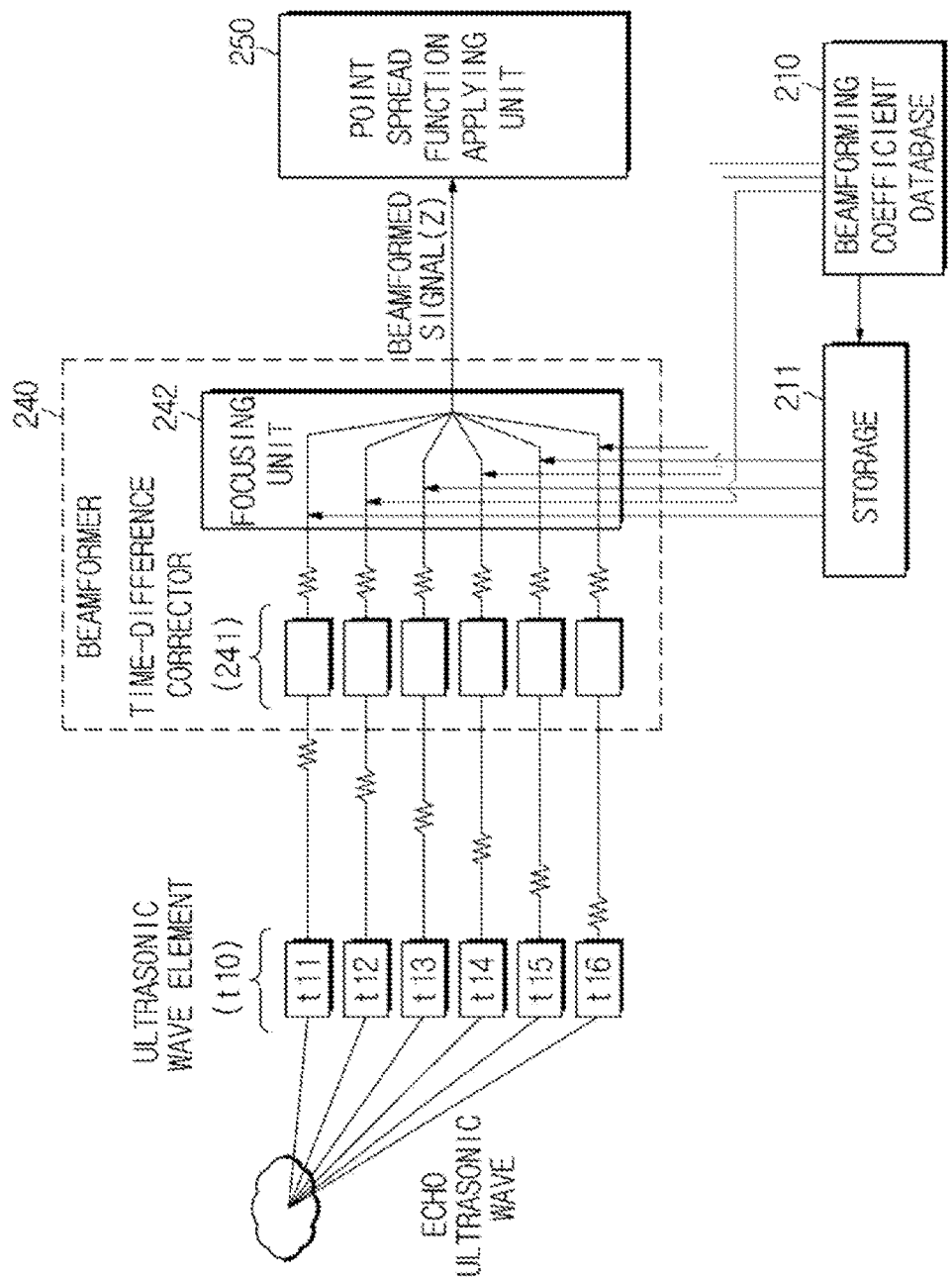
FIG. 9 is a diagram illustrating a configuration of a beamformer according to another exemplary embodiment.

FIG. 9 is a diagram illustrating a configuration of a beamformer according to another exemplary embodiment.

As illustrated in FIG. 9, among ultrasonic signals of a plurality of channels, the focusing unit 242 may use a beamforming coefficient delivered from the storage 211 for ultrasonic signals of some channels, and may use a beamforming coefficient determined by a different way for ultrasonic signals of other channels. In this case, the beamforming coefficient applied to the ultrasonic signals of other channels may be a beamforming coefficient delivered from another unit other than the storage 211, for example, the beamforming coefficient database 210.

In other words, some ultrasonic signals may be focused using at least one beamforming coefficient included in the subgroup selected by the subgroup selector 220, and other ultrasonic signals may be focused using, for example, a predetermined beamforming coefficient or a beamforming coefficient calculated using the ultrasonic signal of a plurality of channels. In this case, the predetermined beamforming coefficient may be a beamforming coefficient selected from among at least one beamforming coefficient stored in the beamforming coefficient database 210. Moreover, using the above Equation 1 or 2, at least one beamforming coefficient is selected from the beamforming coefficient database 210, and then beamforming is performed by applying the at least one selected beamforming coefficient to other ultrasonic signals.

Further, in an ultrasound image corresponding to the ultrasonic signal of a plurality of channels, some areas of the ultrasound image use at least one beamforming coefficient included in the selected subgroup to beamform, and other areas use a beamforming coefficient determined by a different way to beamform, for example, at least one beamforming coefficient selected from the beamforming coefficient database 210.

A signal (z) beamformed by the beamformer 240 may be used as an ultrasound image.

When the coefficient selector 230 calculates the search score, a predetermined ultrasound image may be obtained without ultrasonic signal beamforming by the above beamformer 240. More specifically, when the coefficient selector 230 displays the search score as a log scale, an ultrasound image having a predetermined B mode corresponding to the ultrasonic signal may be obtained.

According to one or more of the exemplary embodiments, as illustrated in FIGS. 8 and 9, the signal (z) beamformed by the beamformer 240 may be delivered to a point spread function applying unit 250. Alternatively, the beamformed signal (z) may be delivered to an image post-processor 260, the image storage 300, or the display unit (d).

The point spread function applying unit 250 may correct the beamformed ultrasonic signal (z) using a point spread function (PSF).

The point spread function may be a function representing a relation between an ideal image and an obtained image signal (RF image data). When an imaging device, for example, the ultrasonic imaging device, captures a predetermined object, there may be a difference between the obtained image signal and the ideal image due to technical or physical characteristics of the imaging device, for example, scratches of the ultrasonic wave element. The point spread function is a function that describes such a difference.

The point spread function applying unit 250 may apply the point spread function, correct the beamformed ultrasonic signal (z), and generate an ultrasound image that is similar to or the same as the ideal image. In this case, the point spread function to be used may be determined by the user or the system designer in advance, or determined depending on the input signal (x) or the beamformed signal (z).

The ultrasound image corrected by the point spread function applying unit 250 may be delivered to the image post-processor 260 or the display unit (d).

A predetermined filter may be additionally applied to the beamformed ultrasonic signal or the ultrasound image to which the point spread function is applied in order to correct the ultrasound image.

The image post-processor 260 may perform predetermined image processing for an ultrasound image generated by an ultrasonic signal generated by the beamformer 240, an ultrasound image obtained by the search score, or an ultrasound image obtained by the point spread function applying unit 250. For example, the image post-processor 260 may correct, for example, brightness, luminance, contrast, or sharpness of all or some of the ultrasound image. The image post-processor 260 may correct all or some of the ultrasound image according to the user instructions or commands, or predefined settings. Moreover, the image post-processor 260 may generate a 3D stereoscopic ultrasound image by combining a plurality of ultrasound images. A synthesized ultrasound image on which predetermined image processing is performed in the image post-processor 260 may be delivered to and stored in the image storage 300, or may be displayed to the user through the display unit (d).

The image storage 300 may temporarily or permanently store the beamformed ultrasonic signal output from the beamformer 240, that is, the beamformed ultrasound image, the ultrasound image obtained by the search score, the ultrasound image output from the point spread function applying unit 250, or a post-processed ultrasound image that is corrected by the image post-processor 260. The ultrasound image stored in the image storage 300 may be delivered to the display unit (d).

The display unit (d) may display, to the user, the beamformed ultrasound image output from the beamformer 240, the ultrasound image obtained by the search score, the ultrasound image output from the point spread function applying unit, the post-processed ultrasound image that is corrected by the image post-processor 260, or the image stored in the image storage 300. According to the exemplary embodiment, as illustrated in FIG. 5, the display unit (d) may be a monitor device provided in the ultrasonic imaging device. According to another exemplary embodiment, the display unit (d) may be connected to or provided in a separate workstation that is connected to the ultrasonic imaging device via a wired or wireless communication network.

Figure 10:
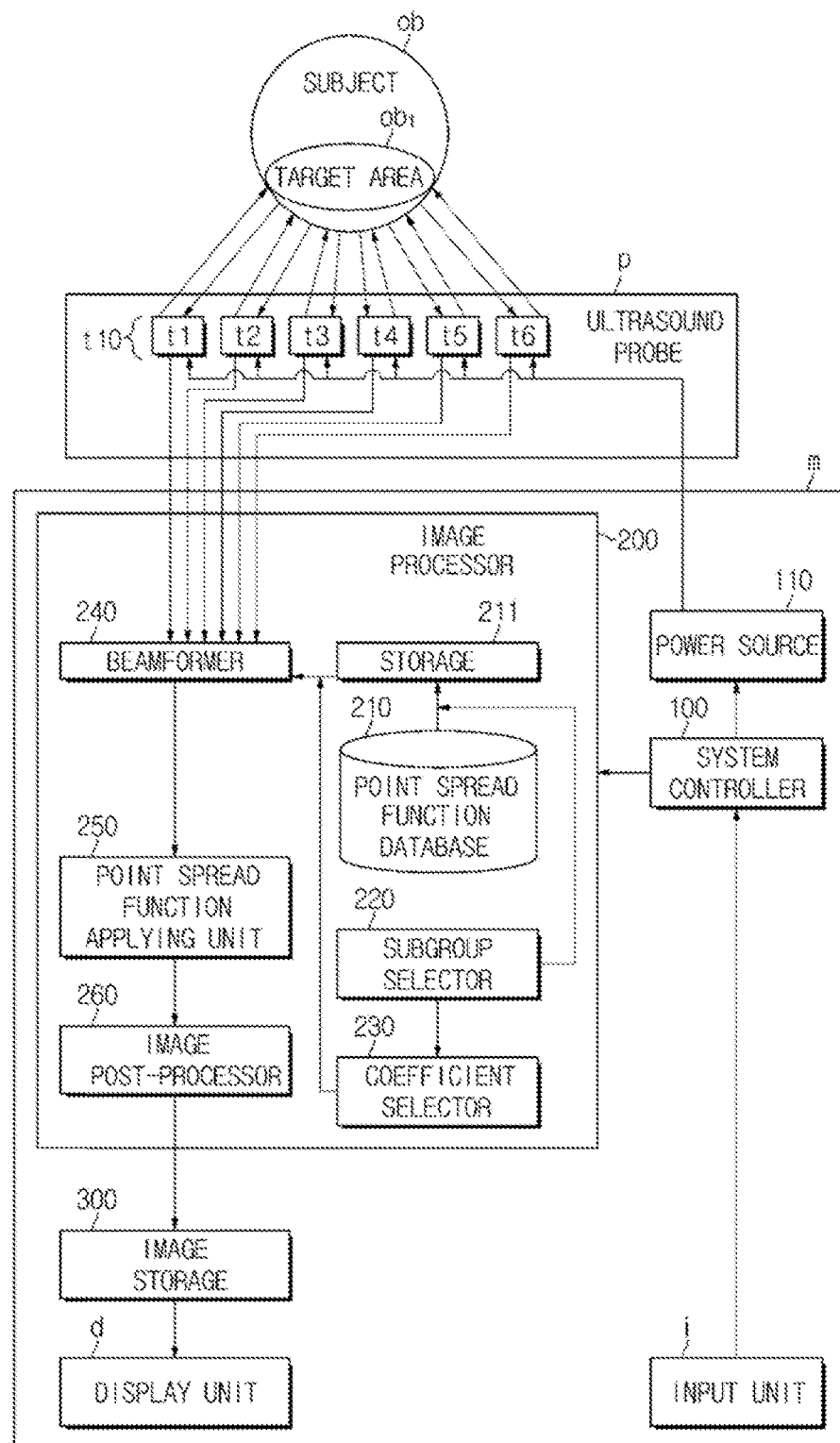
FIG. 10 is a diagram illustrating a configuration of an ultrasonic imaging device according to another exemplary embodiment.

FIG. 10 is a diagram illustrating a configuration of an ultrasonic imaging device according to another exemplary embodiment.

As illustrated in FIG. 10, according to another exemplary embodiment of the ultrasonic imaging device, the image processor 200 of the ultrasonic imaging device may include a point spread function database 210. The point spread function database 210 may include at least one point spread function. In this case, the point spread function of the point spread function database 210 may be included in at least one subgroup. That is, the point spread function database 210 may include at least one subgroup including at least one point spread function.

In this case, the subgroup selector 220 may select at least one subgroup stored in the point spread function database 210, and store the selected subgroup in the storage 211. The coefficient selector 230 may select at least one appropriate point spread function from the at least one subgroup stored in the storage 211. The at least one point spread function selected by the coefficient selector 230 may be delivered to the point spread function applying unit 250. The point spread function applying unit 250 may use the at least one delivered point spread function to obtain an ideal, or near ideal, ultrasound image of the beamformed ultrasonic signal.

Hereinafter, an ultrasonic imaging device control method according to an exemplary embodiment will be described with reference to FIG. 11.

Figure 11:
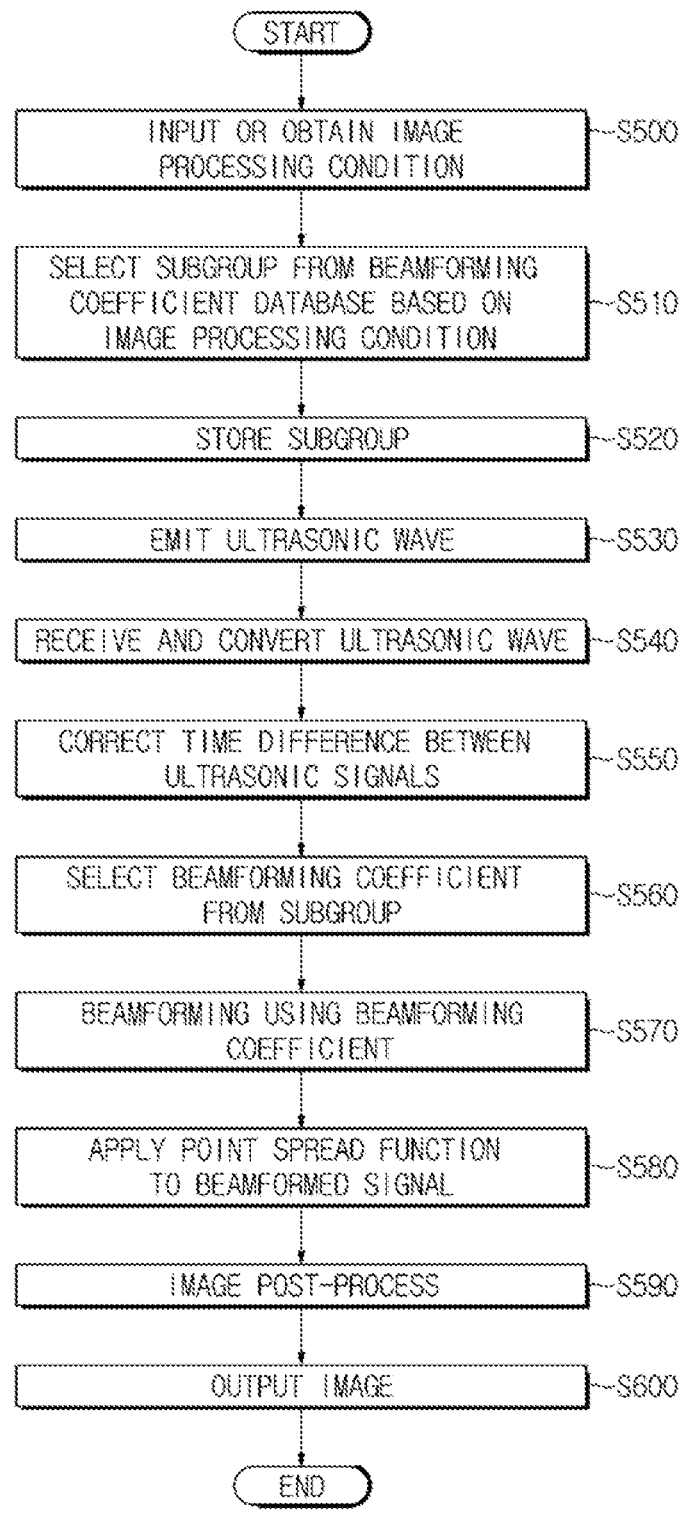
FIG. 11 is a flowchart illustrating an ultrasonic imaging device control method according to an exemplary embodiment.

FIG. 11 is a flowchart illustrating the ultrasonic imaging device control method according to an exemplary embodiment.

As illustrated in FIG. 11, according to an ultrasound image processing control method, a condition for image processing is obtained first, from a user through an input unit, or from a separate storage (s500). In this case, the input or obtained condition may include at least one of an ultrasound image capture mode, a beamforming method, a kind of a subject, a frequency of an ultrasonic wave, and a focus area of an ultrasonic wave. Alternatively, a plurality of conditions may be input and/or obtained.

Subsequently, based on the image processing condition, at least one subgroup is selected from a beamforming coefficient database (s510). In this case, each subgroup may include at least one beamforming coefficient. When a plurality of subgroups are selected, each subgroup may include a mutually different beamforming coefficient, or beamforming coefficients in which some beamforming coefficients are overlapped with another subgroup.

The selected subgroup is stored in a storage such as a cache memory (s520).

Subsequently, an ultrasound probe of an ultrasonic imaging device may emit an ultrasonic wave to a target area inside the subject (s530).

The emitted ultrasonic wave is reflected at the target area inside the subject, the ultrasound probe receives the reflected echo ultrasonic wave, and then converts the received echo ultrasonic wave into an ultrasonic signal of at least one channel and outputs the result (s540). According to the exemplary embodiment, at least one operation of ultrasonic wave emitting operation (s530) and ultrasonic signal output operation (s540) may be performed prior to the above-described operations s510 and s520.

When ultrasonic signals of a plurality of channels are output, a time difference among the ultrasonic signals of a plurality of channels may be corrected (s550). In this case, the ultrasonic signal of each channel is delivered to have a predetermined time delay so that the time difference among the ultrasonic signals of a plurality of channels may be corrected.

At least one beamforming coefficient to be used for focusing the ultrasonic signal of at least one channel is selected and extracted from the subgroup stored in the storage (s560). According to the exemplary embodiment, beamforming coefficient selecting operation (s560) may be performed subsequent to the above storing operation (s520), or prior to time difference correcting operation of the ultrasonic signal (s550).

Subsequently, the ultrasonic signal of at least one channel may be focused using the at least one beamforming coefficient selected from the subgroup (s570). According to exemplary embodiments, at least one beamforming coefficient selected from the subgroup may be applied to ultrasonic signals of all channels input from the ultrasound probe to focus the ultrasonic signals, or may be applied to ultrasonic signals of some channels among ultrasonic signals of all channels input from the ultrasound probe to focus the ultrasonic signals. In the latter case, a separate beamforming coefficient may not be applied to ultrasonic signals of other channels, a beamforming coefficient stored in the beamforming coefficient database may be applied thereto, or a predetermined constant beamforming coefficient may be applied thereto.

As a focusing result of the ultrasonic signals, a beamformed ultrasonic signal, that is, a beamformed ultrasound image, may be obtained.

Subsequently, the point spread function or various filters may be applied to the beamformed ultrasonic signal so that an ultrasound image that is similar to or the same as an ideal image, or a filtered ultrasound image may be obtained (s580).

Predetermined image post-processing may also be performed on the obtained ultrasound image (s590). The ultrasound image on which image post-processing is performed may be stored in a separate storage, or delivered to a display unit such as a monitor device.

The beamformed ultrasound image, the ultrasound image that is similar to or the same as the ideal image, the filtered ultrasound image, or the image on which image post-processing is performed may be output to a display device such as a monitor and be presented to the user (s600).

According to the above image processor, ultrasonic imaging device, and image processing method, it is possible to perform image processing rapidly.

When image processing is performed, the optimal weighting coefficient for image processing may be searched for and selected in a short time. Therefore, it is possible to perform image processing rapidly.

Moreover, it is also possible to search for and select the optimal weighting coefficient in a short time according to, for example, a type or depth of an imaging target, and image signal characteristics.

In addition, the ultrasonic imaging device may obtain an appropriate beamforming coefficient for ultrasonic signal beamforming or an appropriate point spread function for image processing of beamformed signals at a high speed.

Accordingly, resource usage may decrease, a load of the ultrasonic imaging device may decrease, and real time image processing and displaying may be possible.

What is claimed is:

1. An image processing apparatus comprising:
a signal input device configured to receive an input signal on a channel;
a weighting coefficient database configured to store at least one weighting coefficient wherein the at least one weighting coefficient is part of a weighting coefficient subgroup from among a plurality of weighting coefficient subgroups;
a cache memory separate from the weighting coefficient database and configured to store the plurality of weighting coefficient subgroups; and
a processor configured to:
select the plurality of weighting coefficient subgroups from the weighting coefficient database based on an image processing condition, wherein the image processing condition comprises at least one of an image capture mode, an image processing method, and input signal characteristics, and wherein the image processing condition is determined according to input from a user or predefined settings,
store the plurality of weighting coefficient subgroups in the cache memory,
select a weighting coefficient subgroup from among the plurality of weighting coefficient subgroups stored in the cache memory based on a priority,
select the at least one weighting coefficient applied to the input signal from the weighting coefficient subgroup, and
convert the input signal by using the at least one weighting coefficient selected from the weighting coefficient subgroup,
wherein the priority is assigned to the weighting coefficient subgroup with respect to the plurality of weighting coefficient subgroups, and wherein the processor is further configured to select a subgroup having a subsequent priority, when the at least one weighting coefficient is not detected in the weighting, coefficient subgroup.

2. The image processing apparatus according to claim 1, wherein the processor is further configured to store the weighting coefficient subgroup selected from the weighting coefficient database in the cache memory, and convert the input signal by selecting and using the at least one weighting coefficient from the weighting coefficient subgroup stored in the cache memory when image processing is performed.

3. The image processing apparatus according to claim 1, wherein the image processing apparatus is further configured to select the weighting coefficient subgroup from the weighting coefficient database based on at least one of an external input and a condition.

4. The image processing apparatus according to claim 1, wherein the processor is further configured to select the at least one weighting coefficient, for input signals of some channels among input signals of at least one channel, from the weighting coefficient subgroup, and convert the input signals of some channels.

5. An ultrasonic imaging device comprising:
   an ultrasound probe configured to receive an echo ultrasonic wave on a channel from a subject, and convert the received echo ultrasonic wave into an ultrasonic signal of the channel;
   a weighting coefficient database configured to store a plurality of weighting coefficients wherein at least one of the plurality of weighting coefficients corresponds to a weighting coefficient subgroup from among a plurality of weighting coefficient subgroups;
   cache memory separate from the weighting coefficient database and configured to store the plurality of weighting coefficient subgroups; and
   an image processor configured to:
      select the plurality of weighting coefficient subgroups from the weighting coefficient database based on an image processing condition, wherein the image processing condition comprises at least one of an image capture mode, an image processing method, and input signal characteristics, and wherein the image processing condition is determined according to input from a user or predefined settings,
      store the plurality of weighting coefficient subgroup in the cache memory,
      select a weighting coefficient subgroup from among the plurality of weighting coefficient subgroups stored in the cache memory based on a priority,
      select at least one weighting coefficient applied to the ultrasonic signal from the weighting coefficient subgroup, and
      convert the ultrasonic signal by using the at least one weighting coefficient selected from the weighting coefficient subgroup,
   wherein the priority is assigned to the weighting coefficient subgroup with respect to the plurality of weighting coefficient subgroups, and
   wherein the image processor is further configured to select a subgroup having a subsequent priority, when the at least one weighting coefficient is not detected in the weighting coefficient subgroup.

6. The ultrasonic imaging device according to claim 5, wherein the image processor is further configured to store the weighting coefficient subgroup selected from the weighting coefficient database in the cache memory, and convert the input signal by selecting and using the at least one weighting coefficient from the weighting coefficient subgroup stored in the cache memory when image processing is performed.

7. The ultrasonic imaging device according to claim 5, wherein the at least one weighting coefficient is at least one of a beamforming coefficient, a conversion filter, and a point spread function.

8. The ultrasonic imaging device according to claim 5, wherein the image processor is further configured to select at least one weighting coefficient subgroup from the weighting coefficient database based on at least one of an external input and a condition.

9. The ultrasonic imaging device according to claim 8, wherein the condition is at least one of an ultrasound image capture mode, a beamforming method, a kind of a subject, a frequency of an ultrasonic wave, and a focus area of an ultrasonic wave.

10. The ultrasonic imaging device according to claim 5, wherein the image processor is further configured to select the at least one weighting coefficient, for input signals of some channels among input signals of at least one channel, from the weighting coefficient subgroup, and convert the input signals of some channels.

11. An image processing method comprising:
   selecting a plurality of weighting coefficient subgroups from a weighting coefficient database based on an image processing condition, wherein the weighting coefficient subgroup comprises a plurality of weighting coefficients configured to be used with input signals received over at least one channel and to be stored in the weighing coefficient database, and wherein the image processing condition is determined according to input from a user or predefined settings;
   storing the plurality of weighting coefficient subgroups in a cache memory separate from the weighting coefficient database;
   receiving an input signal on the at least one channel;
   select a weighting coefficient subgroup among the plurality of weighting coefficient subgroups stored in the cache memory based on a priority;
   selecting at least one weighting coefficient among the plurality of weighting coefficients applied to the input signal from the selected weighting coefficient subgroup; and
   converting the input signal of the at least one channel using the at least one weighting coefficient selected from the weighting coefficient subgroup,
   wherein the image processing condition comprises at least one of an image capture mode, an image processing method, and input signal characteristics,
   wherein the priority is assigned to the at least one weighting coefficient subgroup with respect to the plurality of weighting coefficient subgroups, and
   selecting a subgroup having a subsequent priority, when the at least one weighting coefficient is not detected in the weighting coefficient subgroup.

12. The image processing method according to claim 11, the storing the weighting coefficient subgroup comprising:
   storing the weighting coefficient subgroup selected from the weighting coefficient database at least one of temporarily and permanently.

13. The image processing method according to claim 11, wherein, in the selecting of the at least one weighting coefficient subgroup, the at least one weighting coefficient subgroup is selected from the weighting coefficient database based on at least one of an external input and a condition.

14. The image processing method according to claim 11, wherein the at least one weighting coefficient is at least one of a beamforming coefficient, a conversion filter, and a point spread function.

15. The image processing apparatus according to claim 1, wherein the processor selects the at least one weighting coefficient by determining that the at least one weighting coefficient minimizes at least one from among a sum of absolute values of the input signal to which a predetermined weighting signal is added, and a sum of absolute values of squares of the input signal to which a predetermined weighting coefficient is added.

16. The image processing apparatus according to claim 1, wherein the input signal characteristics comprise at least one from among a focal length, a frequency of an ultrasonic wave, and a sound wave in the input signal device.

* * * * *